United States Patent
Wan et al.

(10) Patent No.: US 11,564,691 B2
(45) Date of Patent: Jan. 31, 2023

(54) POWERED CIRCULAR STAPLING DEVICE

(71) Applicant: Covidien LP, Mansfield, MA (US)

(72) Inventors: Yanli Wan, Shanghai (CN); Zhaokai Wang, Shanghai (CN); Xiliang Zhang, Shanghai (CN)

(73) Assignee: Covidien LP, Mansfield, MA (US)

( * ) Notice: Subject to any disclaimer, the term of this patent is extended or adjusted under 35 U.S.C. 154(b) by 109 days.

(21) Appl. No.: 17/268,343

(22) PCT Filed: Aug. 24, 2018

(86) PCT No.: PCT/CN2018/102240
§ 371 (c)(1),
(2) Date: Feb. 12, 2021

(87) PCT Pub. No.: WO2020/037649
PCT Pub. Date: Feb. 27, 2020

(65) Prior Publication Data
US 2021/0322013 A1   Oct. 21, 2021

(51) Int. Cl.
*A61B 17/00*   (2006.01)
*A61B 17/115*   (2006.01)

(52) U.S. Cl.
CPC . *A61B 17/1155* (2013.01); *A61B 2017/00398* (2013.01)

(58) Field of Classification Search
CPC . A61B 17/068; A61B 17/1155; A61B 17/072; A61B 2017/00362; A61B 17/115; A61B 17/00
See application file for complete search history.

(56) References Cited

U.S. PATENT DOCUMENTS 3,193,165 A   7/1965   Akhalaya et al.
3,388,847 A   6/1968   Kasulin et al.
(Continued)

FOREIGN PATENT DOCUMENTS

CA   908529 A   8/1972
CA   2805365 A1   8/2013
(Continued)

OTHER PUBLICATIONS

Extended European Search Report dated Jun. 15, 2022, issued in corresponding EP Appln. No. 18930622, 16 pages.
(Continued)

*Primary Examiner* — Gloria R Weeks
(74) *Attorney, Agent, or Firm* — Carter, DeLuca & Farrell LLP

(57) ABSTRACT

A powered circular stapling device (10) includes a transfer switch assembly (90) for a transmission assembly (40) to selectively direct power between clamping and firing mechanisms of the stapling device (10). The transfer switch assembly (90) includes a carriage (92), a worm gear assembly (94), and first and second biasing mechanisms (96). The worm gear assembly (94) is supported on the carriage (92) and movable in relation to the carriage (92) to allow the worm gear assembly (94) to engage with a first or second gear (44, 46) of the transmission assembly (40). The biasing mechanisms (96) allow the worm gear assembly (94) to move in relation to the carriage (92) when the gear teeth of the worm gear (94) are misaligned with the gear teeth of one of the first and second gears (44, 46) of the transmission assembly (40), to allow the gear teeth of the worm gear (94) to move into alignment with the gear teeth of the other one of the first and second gears (44, 46) of the transmission assembly (40).

16 Claims, 14 Drawing Sheets

(56) References Cited

U.S. PATENT DOCUMENTS

| | | |
|---|---|---|
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Faheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,144 A | 11/1995 | Guy et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,041,462 A * | 3/2000 | Marques ............... A46B 13/008 134/140 |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Billner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |

(56) References Cited

U.S. PATENT DOCUMENTS

| | | |
|---|---|---|
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Dell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,458,295 B1 * | 12/2008 | Lu .................. B25B 21/004 81/63 |
| 7,481,347 B2 | 1/2009 | Roy |
| 7,494,038 B2 | 2/2009 | Milliman |
| 7,506,791 B2 | 3/2009 | Omaits et al. |
| 7,510,107 B2 * | 3/2009 | Timm ............. A61B 17/07207 227/176.1 |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |

(56) References Cited

U.S. PATENT DOCUMENTS

| | | | |
|---|---|---|---|
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 3,002,795 A1 | 8/2011 | Beetel |
| 3,006,701 A1 | 8/2011 | Bilotti et al. |
| 3,006,889 A1 | 8/2011 | Adams et al. |
| 3,011,551 A1 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,479,968 B2 | 7/2013 | Hodgkinson et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,627,995 B2 | 1/2014 | Smith et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,646,674 B2 | 2/2014 | Schulte et al. |
| 8,662,370 B2 | 3/2014 | Takei |
| 8,663,258 B2 | 3/2014 | Bettuchi et al. |
| 8,672,207 B2 | 3/2014 | Shelton, IV et al. |
| 8,672,931 B2 | 3/2014 | Goldboss et al. |
| 8,672,951 B2 | 3/2014 | Smith et al. |
| 8,678,264 B2 | 3/2014 | Racenet et al. |
| 8,679,137 B2 | 3/2014 | Bauman et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,695,864 B1 | 4/2014 | Hausen |
| 8,708,212 B2 | 4/2014 | Williams |
| 8,733,611 B2 | 5/2014 | Milliman |
| 8,733,615 B2 | 5/2014 | Nalagatla et al. |
| 8,746,531 B2 | 6/2014 | Wenchell et al. |
| 8,746,532 B2 | 6/2014 | Nalagatla et al. |
| 8,783,543 B2 | 7/2014 | Shelton, IV et al. |
| 8,789,737 B2 | 7/2014 | Hodgkinson et al. |
| 8,800,838 B2 | 8/2014 | Shelton, IV |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,821,523 B2 | 9/2014 | Heinrich et al. |
| 8,827,903 B2 | 9/2014 | Shelton, IV et al. |
| 8,833,629 B2 | 9/2014 | Nalagatla et al. |
| 8,840,004 B2 | 9/2014 | Holsten et al. |
| 8,844,792 B2 | 9/2014 | Viola |
| 8,845,661 B2 | 9/2014 | D'Arcangelo et al. |
| 8,870,911 B2 | 10/2014 | Williams et al. |
| 8,875,974 B2 | 11/2014 | Rebuffat et al. |
| 8,893,948 B2 | 11/2014 | Williams |
| 8,910,847 B2 | 12/2014 | Nalagatla et al. |
| 8,925,785 B2 | 1/2015 | Holsten et al. |
| 8,925,786 B2 | 1/2015 | Holsten et al. |
| 8,967,448 B2 | 3/2015 | Carter et al. |
| 8,978,955 B2 | 3/2015 | Aronhalt et al. |
| 9,010,608 B2 | 4/2015 | Casasanta, Jr. et al. |
| 9,010,612 B2 | 4/2015 | Stevenson et al. |
| 9,016,540 B2 | 4/2015 | Whitman et al. |
| 9,629,633 B2 * | 4/2017 | Williams ............. A61B 17/072 |
| 9,649,110 B2 * | 5/2017 | Parihar ............. A61B 17/1155 |
| 10,433,848 B2 | 10/2019 | Chen et al. |
| 10,456,134 B2 | 10/2019 | DiNardo et al. |
| 10,463,365 B2 | 11/2019 | Williams |
| 10,463,373 B2 | 11/2019 | Mozdzierz et al. |
| 10,463,374 B2 | 11/2019 | Sgroi, Jr. |
| 10,470,770 B2 | 11/2019 | Shelton, IV et al. |
| 10,470,771 B2 | 11/2019 | D'Agostino et al. |

(56) References Cited

U.S. PATENT DOCUMENTS

| | | | |
|---|---|---|---|
| 10,499,922 B2 | 12/2019 | Sgroi, Jr. | |
| 10,506,920 B2 | 12/2019 | Hasser et al. | |
| 10,507,039 B2 | 12/2019 | Williams | |
| 10,508,720 B2 * | 12/2019 | Nicholas | F16H 57/038 |
| 10,512,467 B2 | 12/2019 | Swayze et al. | |
| 10,524,795 B2 | 1/2020 | Nalagatla et al. | |
| 10,524,798 B2 | 1/2020 | Williams | |
| 10,524,868 B2 | 1/2020 | Cooper et al. | |
| 10,537,331 B2 | 1/2020 | Scirica et al. | |
| 10,542,993 B2 | 1/2020 | Guerrera et al. | |
| 10,548,598 B2 | 2/2020 | Prescott et al. | |
| 10,561,424 B2 | 2/2020 | Penna et al. | |
| 10,568,631 B2 | 2/2020 | Rebuffat et al. | |
| 10,575,847 B2 | 3/2020 | Hessler et al. | |
| 10,595,871 B2 | 3/2020 | Racenet et al. | |
| 10,595,872 B2 | 3/2020 | Milliman | |
| 10,603,042 B2 | 3/2020 | Sgroi | |
| 10,617,411 B2 * | 4/2020 | Williams | F16H 25/20 |
| 10,624,646 B2 | 4/2020 | Bae et al. | |
| 10,639,041 B2 | 5/2020 | Williams | |
| 10,653,414 B2 | 5/2020 | Williams | |
| 2003/0111507 A1 | 6/2003 | Nunez | |
| 2005/0051597 A1 | 3/2005 | Toledano | |
| 2005/0107813 A1 | 5/2005 | Gilete Garcia | |
| 2005/0245851 A1 * | 11/2005 | Ferber | A61H 23/0263 601/87 |
| 2006/0000869 A1 | 1/2006 | Fontayne | |
| 2006/0011698 A1 | 1/2006 | Okada et al. | |
| 2006/0201989 A1 | 9/2006 | Ojeda | |
| 2006/0289601 A1 * | 12/2006 | Orban, III | A61B 17/115 227/176.1 |
| 2007/0027473 A1 | 2/2007 | Vresh et al. | |
| 2007/0029363 A1 | 2/2007 | Popov | |
| 2007/0060952 A1 | 3/2007 | Roby et al. | |
| 2008/0255413 A1 | 10/2008 | Zemlok et al. | |
| 2009/0236392 A1 | 9/2009 | Cole et al. | |
| 2009/0236398 A1 | 9/2009 | Cole et al. | |
| 2009/0236401 A1 | 9/2009 | Cole et al. | |
| 2010/0019016 A1 | 1/2010 | Edoga et al. | |
| 2010/0051668 A1 | 3/2010 | Milliman et al. | |
| 2010/0084453 A1 | 4/2010 | Hu | |
| 2010/0147923 A1 | 6/2010 | D'Agostino et al. | |
| 2010/0163598 A1 | 7/2010 | Belzer | |
| 2010/0224668 A1 | 9/2010 | Fontayne et al. | |
| 2010/0230465 A1 | 9/2010 | Smith et al. | |
| 2010/0258611 A1 | 10/2010 | Smith et al. | |
| 2010/0264195 A1 | 10/2010 | Bettuchi | |
| 2010/0327041 A1 | 12/2010 | Milliman et al. | |
| 2011/0011916 A1 | 1/2011 | Levine | |
| 2011/0114697 A1 | 5/2011 | Baxter, III et al. | |
| 2011/0114700 A1 | 5/2011 | Baxter, III et al. | |
| 2011/0144640 A1 | 6/2011 | Heinrich et al. | |
| 2011/0192882 A1 | 8/2011 | Hess et al. | |
| 2012/0145755 A1 | 6/2012 | Kahn | |
| 2012/0193395 A1 | 8/2012 | Pastorelli et al. | |
| 2012/0193398 A1 | 8/2012 | Williams et al. | |
| 2012/0232339 A1 | 9/2012 | Csiky | |
| 2012/0273548 A1 | 11/2012 | Ma et al. | |
| 2012/0325888 A1 | 12/2012 | Qiao et al. | |
| 2013/0015232 A1 | 1/2013 | Smith et al. | |
| 2013/0020372 A1 | 1/2013 | Jankowski et al. | |
| 2013/0020373 A1 | 1/2013 | Smith et al. | |
| 2013/0032628 A1 | 2/2013 | Li et al. | |
| 2013/0060258 A1 | 3/2013 | Giacomantonio | |
| 2013/0105544 A1 | 5/2013 | Mozdzierz et al. | |
| 2013/0105546 A1 | 5/2013 | Milliman et al. | |
| 2013/0105551 A1 | 5/2013 | Zingman | |
| 2013/0126580 A1 | 5/2013 | Smith et al. | |
| 2013/0153630 A1 | 6/2013 | Miller et al. | |
| 2013/0153631 A1 | 6/2013 | Vasudevan et al. | |
| 2013/0153638 A1 | 6/2013 | Carter et al. | |
| 2013/0153639 A1 | 6/2013 | Hodgkinson et al. | |
| 2013/0175315 A1 | 7/2013 | Milliman | |
| 2013/0175318 A1 | 7/2013 | Felder et al. | |
| 2013/0175319 A1 | 7/2013 | Felder et al. | |
| 2013/0175320 A1 | 7/2013 | Mandakolathur Vasudevan et al. | |
| 2013/0181035 A1 | 7/2013 | Milliman | |
| 2013/0181036 A1 | 7/2013 | Olson et al. | |
| 2013/0193185 A1 | 8/2013 | Patel | |
| 2013/0193187 A1 | 8/2013 | Milliman | |
| 2013/0193190 A1 | 8/2013 | Carter et al. | |
| 2013/0193192 A1 | 8/2013 | Casasanta, Jr. et al. | |
| 2013/0200131 A1 | 8/2013 | Racenet et al. | |
| 2013/0206816 A1 | 8/2013 | Penna | |
| 2013/0214027 A1 | 8/2013 | Hessler et al. | |
| 2013/0214028 A1 | 8/2013 | Patel et al. | |
| 2013/0228609 A1 | 9/2013 | Kostrzewski | |
| 2013/0240597 A1 | 9/2013 | Milliman et al. | |
| 2013/0240600 A1 | 9/2013 | Bettuchi | |
| 2013/0248581 A1 | 9/2013 | Smith et al. | |
| 2013/0277411 A1 | 10/2013 | Hodgkinson et al. | |
| 2013/0277412 A1 | 10/2013 | Gresham et al. | |
| 2013/0284792 A1 | 10/2013 | Ma | |
| 2013/0292449 A1 | 11/2013 | Bettuchi et al. | |
| 2013/0299553 A1 | 11/2013 | Mozdzierz | |
| 2013/0299554 A1 | 11/2013 | Mozdzierz | |
| 2013/0306701 A1 | 11/2013 | Olson | |
| 2013/0306707 A1 | 11/2013 | Viola et al. | |
| 2014/0008413 A1 | 1/2014 | Williams | |
| 2014/0012317 A1 | 1/2014 | Orban et al. | |
| 2014/0046352 A1 | 2/2014 | Reboa et al. | |
| 2014/0158747 A1 | 6/2014 | Measamer et al. | |
| 2014/0166717 A1 | 6/2014 | Swayze et al. | |
| 2014/0284370 A1 | 9/2014 | Sahin | |
| 2015/0083772 A1 | 3/2015 | Miller et al. | |
| 2015/0173763 A1 | 6/2015 | Liu | |
| 2015/0209045 A1 | 7/2015 | Hodgkinson et al. | |
| 2016/0143641 A1 | 5/2016 | Sapienza et al. | |
| 2016/0157856 A1 | 6/2016 | Williams et al. | |
| 2016/0302792 A1 | 10/2016 | Motai | |
| 2017/0281187 A1 * | 10/2017 | Shelton, IV | A61B 17/1155 |
| 2019/0247032 A1 * | 8/2019 | Xu | A61B 17/00234 |

FOREIGN PATENT DOCUMENTS

| | | |
|---|---|---|
| CN | 104039244 A | 9/2014 |
| CN | 104042288 A | 9/2014 |
| CN | 104257409 A | 1/2015 |
| CN | 104367360 A | 2/2015 |
| CN | 104918564 A | 9/2015 |
| CN | 105455864 A | 4/2016 |
| CN | 106037851 A | 10/2016 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 2792306 A2 | 10/2014 |
| EP | 3225176 A1 | 10/2017 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |

(56) References Cited

FOREIGN PATENT DOCUMENTS

WO     02080781  A2   10/2002
WO    2008107918 A1    9/2008

OTHER PUBLICATIONS

Partial Supplementary European Search Report dated Mar. 10, 2022, issued in corresponding EP Appln. No. 18930622, 18 pages.
International Search Report dated May 23, 2019, issued in corresponding International Appln. No PCT/CN2018/102240, 4 pages.

* cited by examiner

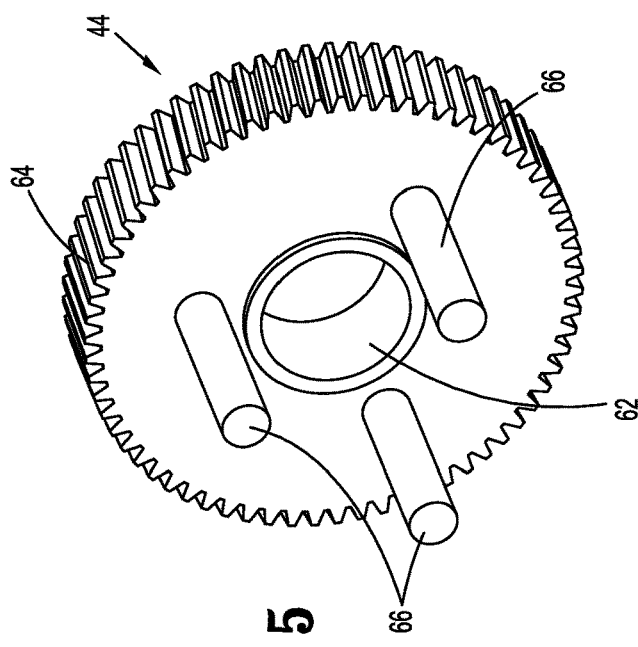
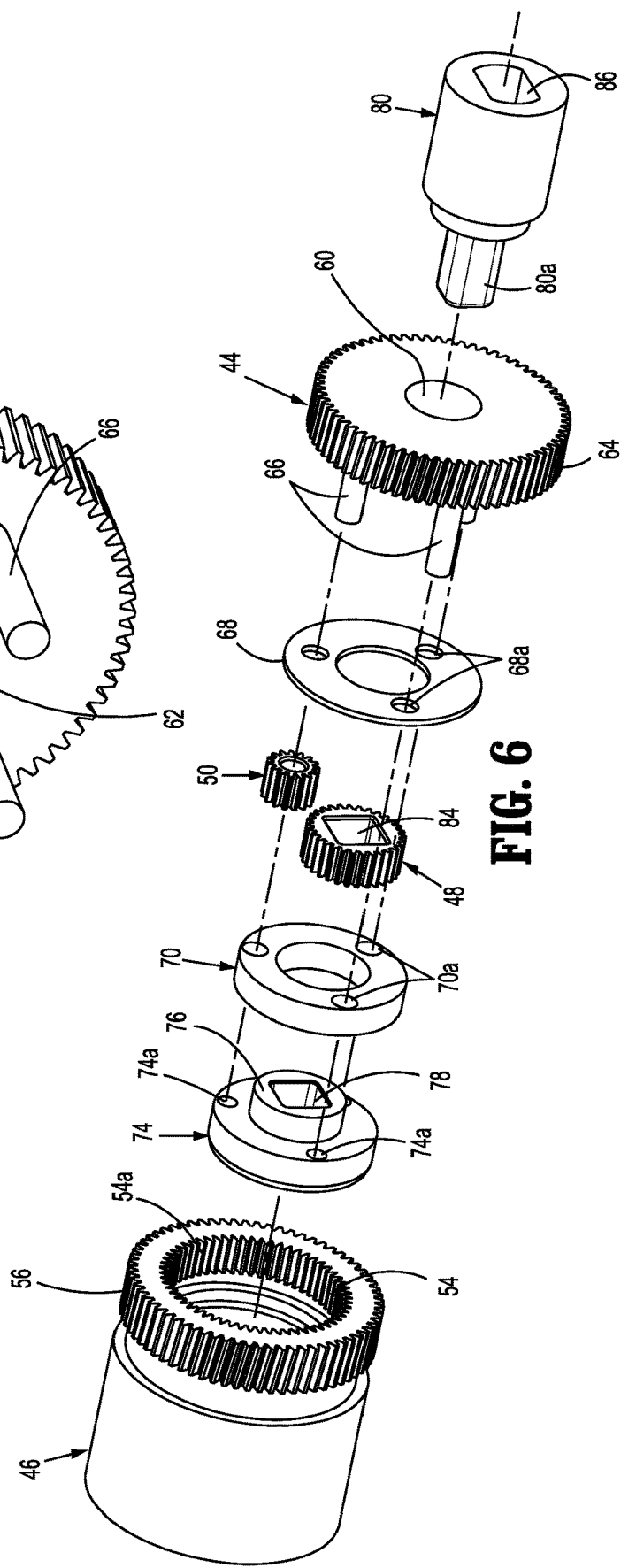

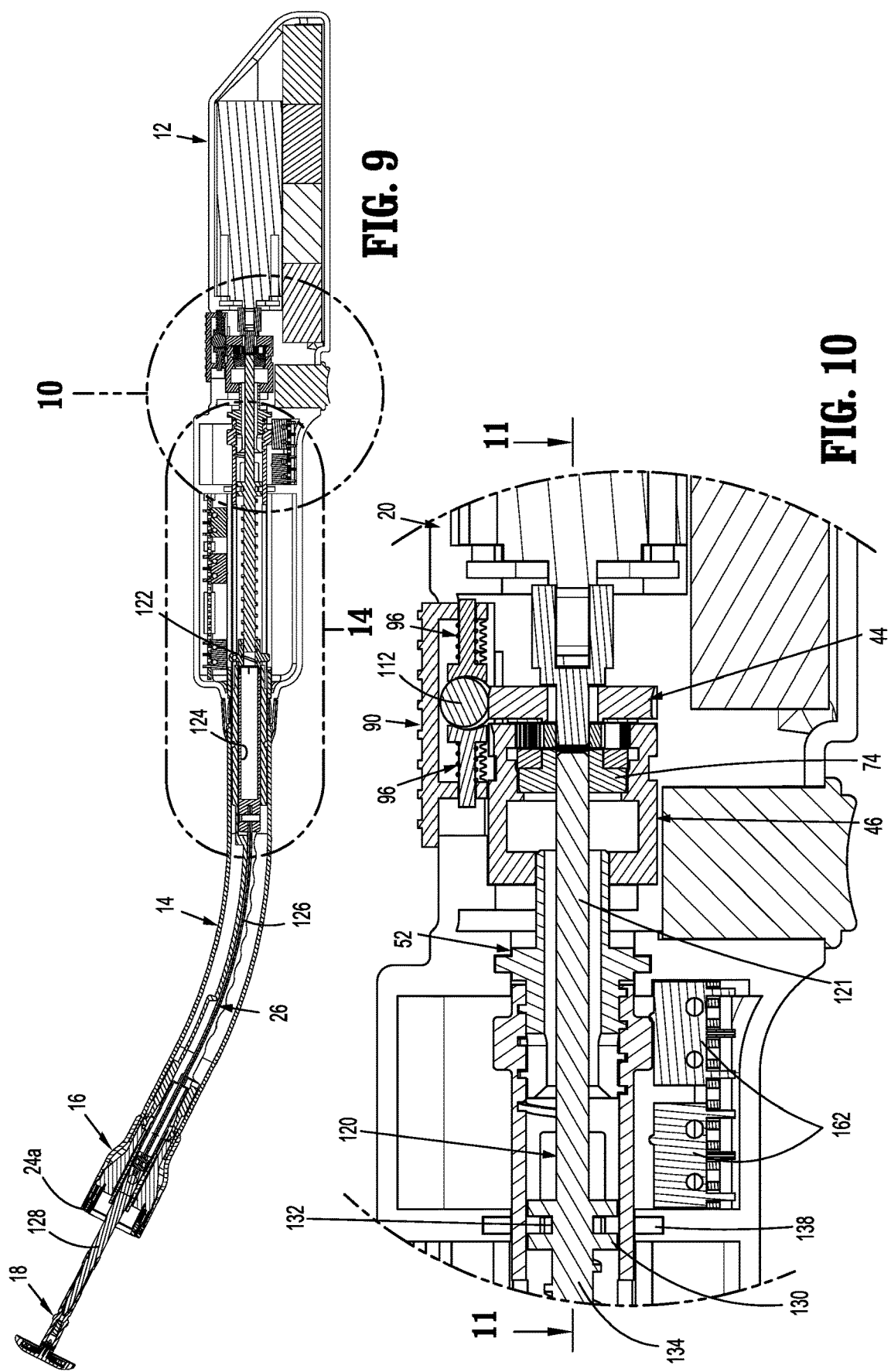

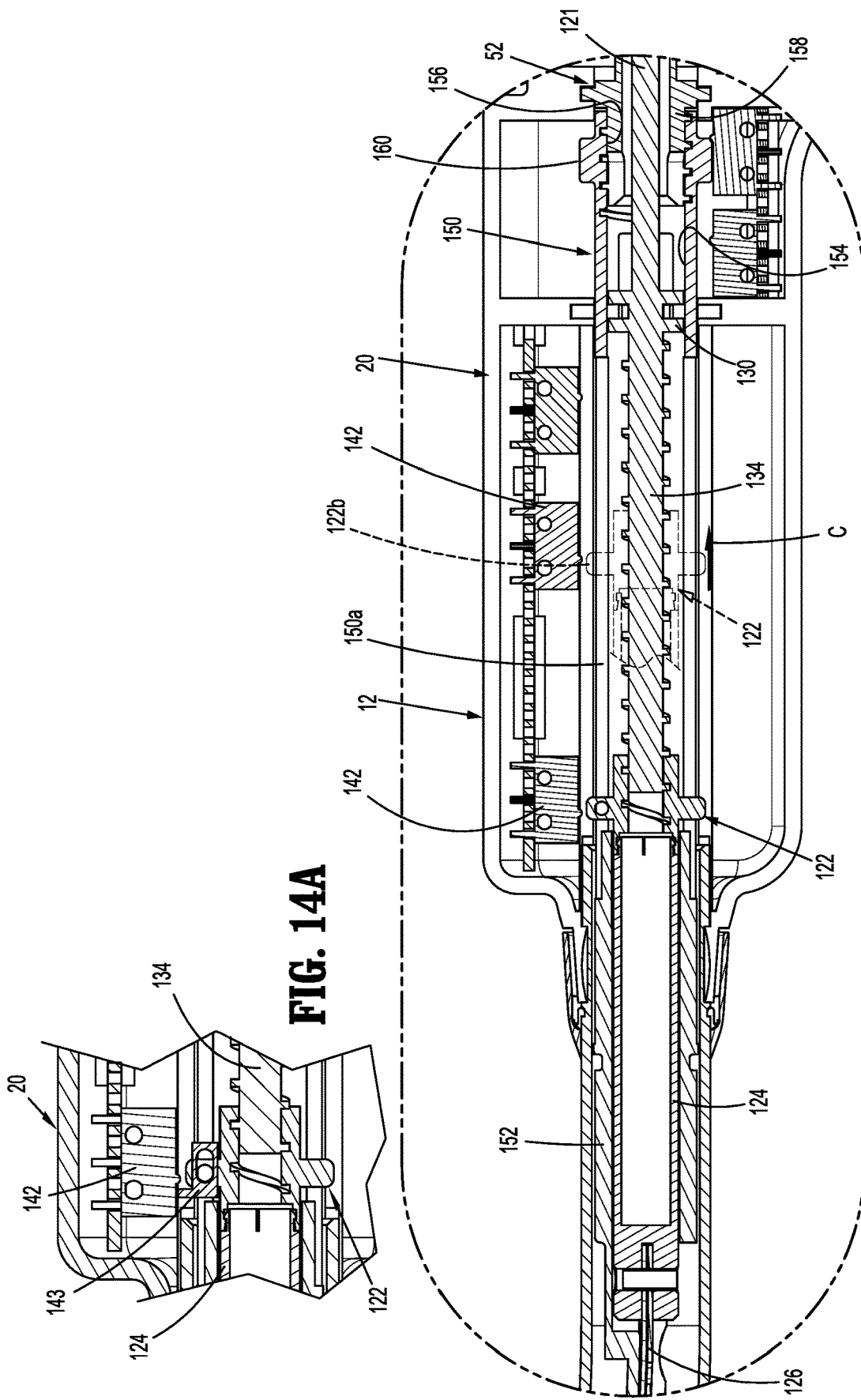

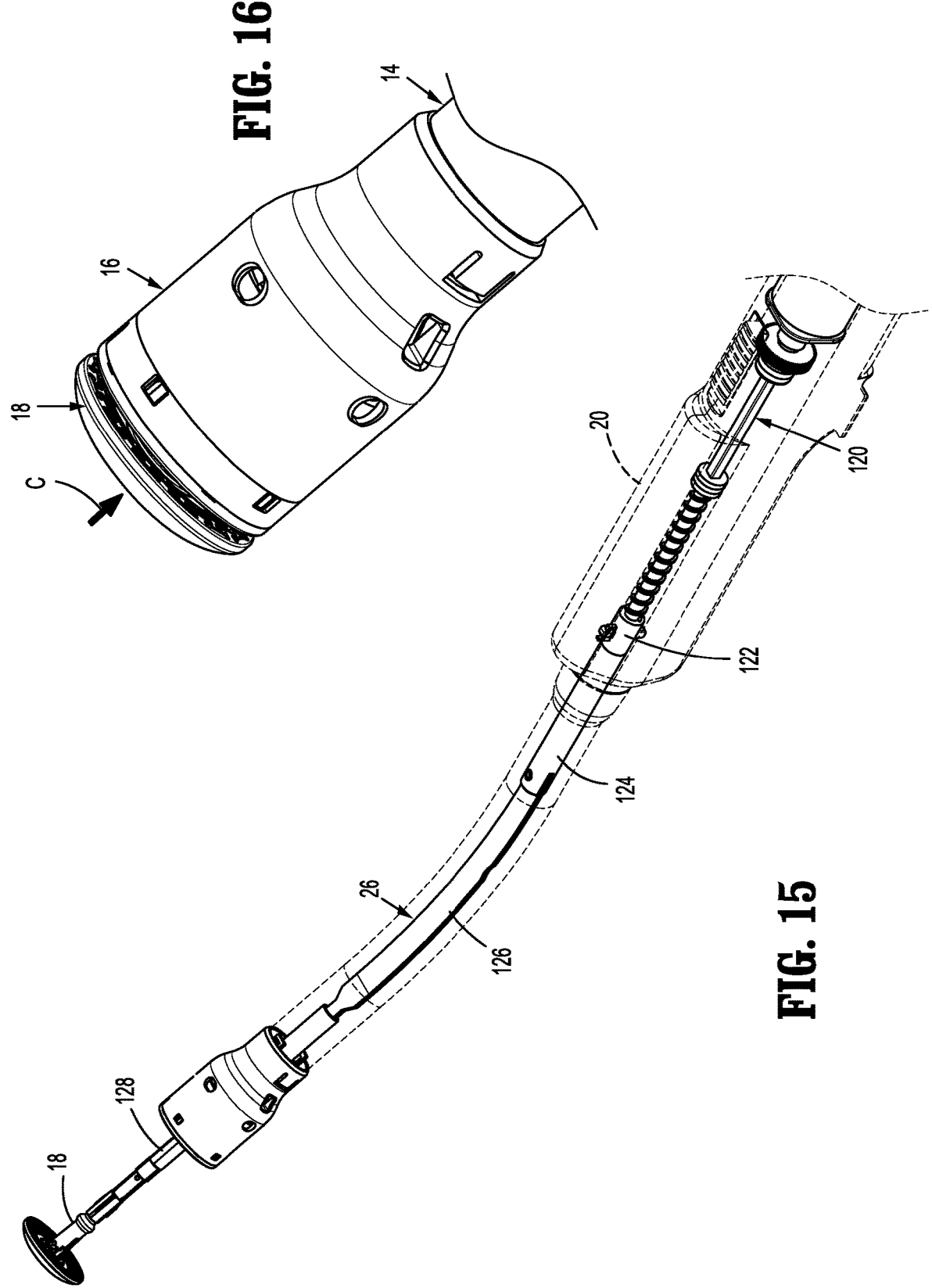

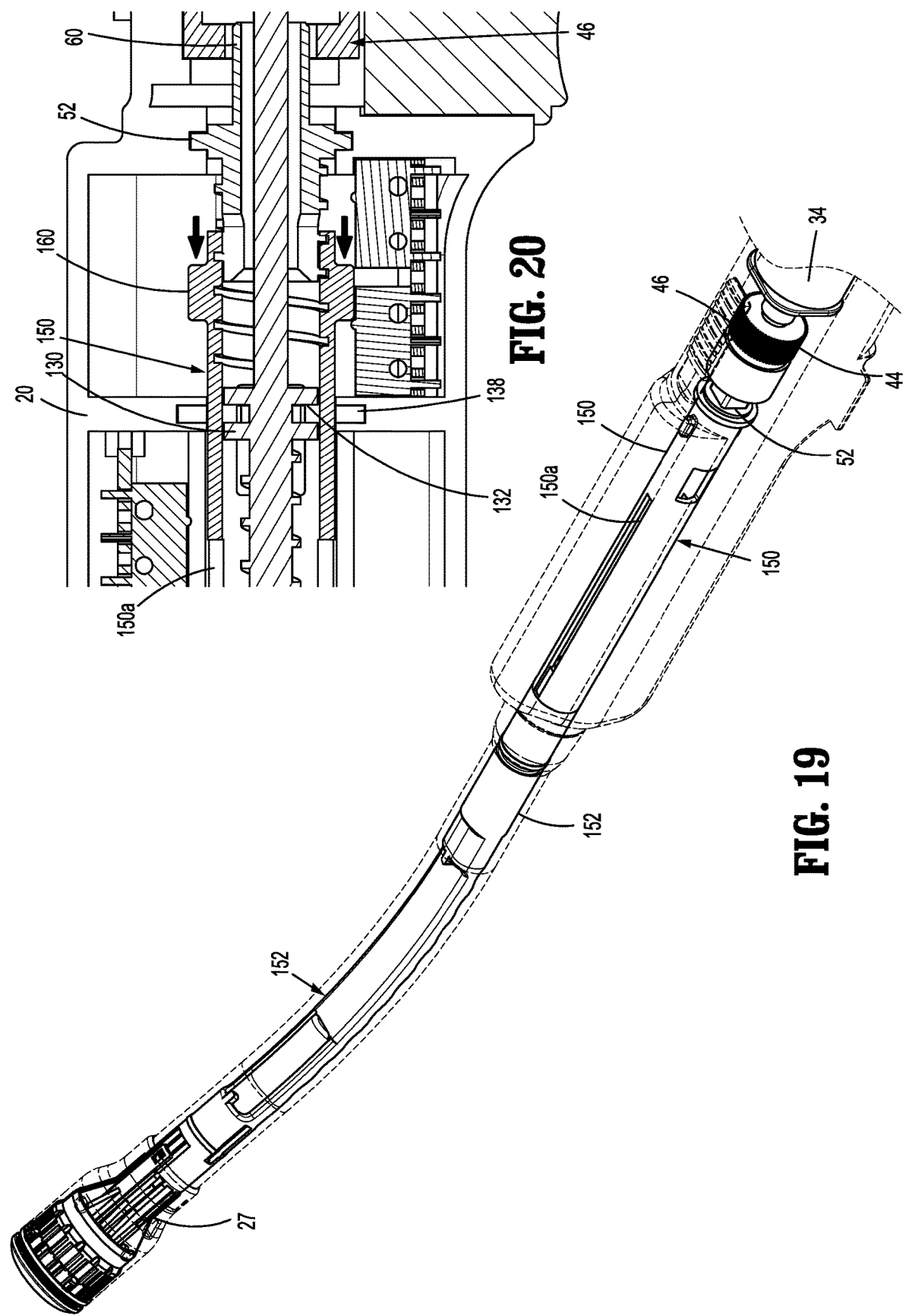

POWERED CIRCULAR STAPLING DEVICE

BACKGROUND

1. Technical Description

The present disclosure is directed to a powered circular stapling device and more particularly to a powered circular stapling device including a transfer switch assembly for a transmission assembly to selectively direct power between clamping and firing mechanisms of the stapling device.

2. Background of Related Art

Surgical stapling devices include a cartridge assembly and an anvil assembly and are commonly used to cut and staple tissue during surgical procedures. The use of surgical stapling devices are preferred over manually cutting and suturing tissue during certain surgical procedures because the stapling procedure can be performed non-invasively and is faster than traditional suturing procedures. Thus, stapling procedures can minimize the time required to perform the surgical procedure while reducing trauma to the patient.

Surgical stapling devices are available in manually actuated configurations as well as powered configurations. Powered surgical staplers typically include a first different drive mechanism for approximating the anvil and cartridge assemblies, a second drive mechanism for firing staples from the cartridge assembly, a motor for actuating the first and second drive mechanisms, and a transmission assembly for selectively interconnecting the motor with one of the first and second drive assemblies.

A continuing need exists in the art for a simple but reliable switch for selectively controlling a transmission assembly to selectively coupling a motor of a surgical stapling device to a approximation assembly or a firing assembly.

SUMMARY

One aspect of the present disclosure is directed to a circular stapling device including a handle assembly, a transfer switch assembly, an elongate body, a shell assembly, and an anvil assembly. The handle assembly includes a housing defining a cavity, a motor, and a transmission assembly. The motor is supported within the cavity and has a drive shaft that is coupled to the transmission assembly. The transmission assembly includes a fire gear, a clamp gear, a sun gear, and a planetary gear. The fire gear includes an annular body having an internal gear surface and an external gear surface. The clamp gear includes an external gear surface and at least one post that rotatably supports the planetary gear. The drive shaft of the motor is coupled to the sun gear, the sun gear is engaged with the planetary gear, and the planetary gear is engaged with the internal gear surface of the fire gear. The transfer switch assembly is supported by the housing of the handle assembly and is movable between a first position engaged with the fire gear to prevent rotation of the fire gear and a second position engaged with the clamp gear to prevent rotation of the clamp gear. The elongate body has a proximal portion coupled to the handle assembly and a distal portion that supports the shell assembly. The shell assembly includes a staple cartridge having an annular array of staples and a pusher. The anvil assembly is operably coupled to the clamp gear and the pusher is operably coupled to the fire gear. The transmission assembly is configured such that when the transfer switch assembly is in the first position, activation of the motor causes movement of the anvil assembly in relation to the staple cartridge, and when the transfer switch assembly is in the second position, activation of the motor causes movement of the pusher in relation to the staple cartridge to eject the annular array of staples from the staple cartridge.

In embodiments, the transfer switch assembly includes a worm gear assembly including a worm gear that is engaged with the fire gear when the transfer switch is in the first position and engaged with the clamp gear when the transfer switch is in the second position.

In some embodiments, the transfer switch assembly includes a carriage supported by the housing of the handle assembly, wherein the carriage is movable in relation to the transmission assembly to move the transfer switch assembly between the first and second positions.

In certain embodiments, the worm gear assembly includes a support gear positioned on each end of the worm gear and the carriage includes spaced racks, wherein the support gears are movable on the spaced racks to support the worm gear on the carriage.

In embodiments, the transfer switch assembly includes first and second biasing mechanisms supported on the carriage. The first biasing mechanism is positioned to engage a first side of the worm gear assembly to urge the worm gear assembly in a first direction and the second biasing mechanism is positioned to engage a second side of the worm gear assembly opposite of the first side of the worm gear assembly to urge the worm gear assembly in a second direction opposite to the first direction. The first and second biasing mechanism are adapted to allow the worm gear assembly to move in relation to the carriage when the worm gear is misaligned with the external gear surface of one of the fire gear and the clamp gear as the transfer switch assembly is moved between the first and second positions.

In some embodiments, the spaced racks include rack teeth that are engaged with the support gears of the worm gear assembly to cause rotation of the support gears when the carriage is moved in relation to the worm gear assembly, wherein rotation of the support gears causes rotation of the worm gear to move the worm gear into alignment with the external gear surface of the fire gear or the clamp gear as the transfer switch assembly is moved between the first and second positions.

In certain embodiments, the transmission assembly further includes a clamping disk and the clamp gear includes a plurality of posts, wherein the planetary gear is supported on one of the plurality of posts and the plurality of posts extend through the clamping disk to secure the clamping disk to the clamp gear such that rotation of the clamp gear causes rotation of the clamping disk.

In embodiments, the clamping disk is coupled to a clamping rod and the clamping rod supports a clamping member. The clamping rod has a distal threaded portion and the clamping member defines a threaded bore, wherein the distal threaded portion of the clamping rod is received within the threaded bore of the clamping member such that rotation of the clamping rod causes longitudinal movement of the clamping member. In embodiments, the clamping member is coupled to the anvil assembly such that longitudinal movement of the clamping member causes longitudinal movement of the anvil assembly.

In some embodiments, the fire gear is coupled to a firing drive member such that rotation of the fire gear causes rotation of the firing drive member.

In certain embodiments, a firing connector defines a threaded bore, wherein the firing drive member includes a threaded distal portion that is received within the threaded bore of the firing connector such that rotation of the firing drive member causes longitudinal movement of the connector extension. In embodiments, the connector extension is coupled to the pusher.

In embodiments, the handle assembly includes a limit switch positioned to limit movement of the firing connector within the housing.

In some embodiments, the handle assembly includes batteries to power the motor.

In certain embodiments, the carriage includes a finger engagement member including an engagement surface that is supported on an outer surface of the housing.

In embodiments, the finger engagement member is supported on an outer surface of the housing.

In some embodiments, the handle assembly includes a limit switch that is positioned to limit movement of the clamping member within the housing.

Another aspect of the disclosure is directed to a transfer switch assembly including a carriage, a worm gear assembly, and first and second biasing mechanisms. The carriage has first and second spaced end walls, a finger engagement member that extends between an upper end of the first and second end walls, and spaced racks that extend between lower ends of the spaced end walls. The worm gear assembly is positioned between the spaced racks and includes a worm gear having gear teeth, and a support gear positioned on each end of the worm gear. The support gears are movable on the spaced racks to movably support the worm gear between the spaced racks on the carriage. The first and second biasing mechanisms are supported on the carriage. The first biasing mechanism is positioned to engage a first side of the worm gear assembly to urge the worm gear assembly in a first direction on the carriage and the second biasing mechanism is positioned to engage a second side of the worm gear assembly opposite to the first side of the worm gear assembly to urge the worm gear assembly in a second direction on the carriage opposite to the first direction.

In embodiments, the carriage is configured to move in relation to a transmission assembly of a device between a first position in which the gear teeth of the worm gear are engaged with gear teeth of a first gear of the transmission assembly and a second position in which the gear teeth of the worm gear are engaged with gear teeth of a second gear of the transmission assembly.

In certain embodiments, the first and second biasing mechanisms are configured to allow the worm gear assembly to move in relation to the carriage when the gear teeth of the worm gear are misaligned with the gear teeth of the first second gears of the transmission assembly, wherein movement of the carriage in relation to the worm gear assembly causes rotation of the support gears to rotate the gear teeth of the worm gear into alignment with the gear teeth of one of the first and second gears of the transmission assembly.

BRIEF DESCRIPTION OF THE DRAWINGS

Various embodiments of the presently disclosed powered circular stapling device are described herein below with reference to the drawings, wherein:

FIG. 5 is a side perspective view of a clamp gear of a transmission assembly of the handle assembly shown in FIG. 4;

FIG. 6 is an enlarged view of the indicated area of detail shown in FIG. 4;

FIG. 9 is a cross-sectional view taken along section line 9-9 of FIG. 1;

FIG. 10 is an enlarged view of the indicated area of detail shown in FIG. 9;

FIG. 14 is an enlarged view of the indicated area of detail shown in FIG. 9;

FIG. 14A is an enlarged view of a clamping limit switch of the handle assembly shown in FIG. 14;

FIG. 15 is a side perspective view of the stapling device shown in FIG. 1 with the handle housing and elongate body of the stapling device shown in phantom illustrating a clamping mechanism of the stapling device with the stapling device in an unclamped position;

FIG. 16 is a side perspective view of a distal portion of the stapling device shown in FIG. 1 as an anvil assembly of the stapling device is moved towards a staple cartridge of the stapling device to position the stapling device in the clamped position;

FIG. 19 is a side perspective view of the stapling device shown in FIG. 1 with the handle housing and the elongate body of the stapling device shown in phantom illustrating a firing mechanism of the stapling device with the stapling device in the clamped position; and FIG. 20 is a side cross-sectional view taken through a portion of the handle assembly as a firing connector of the firing transmission assembly shown in FIG. 4 is advanced within the handle assembly.

DETAILED DESCRIPTION OF EMBODIMENTS

Figure 1:
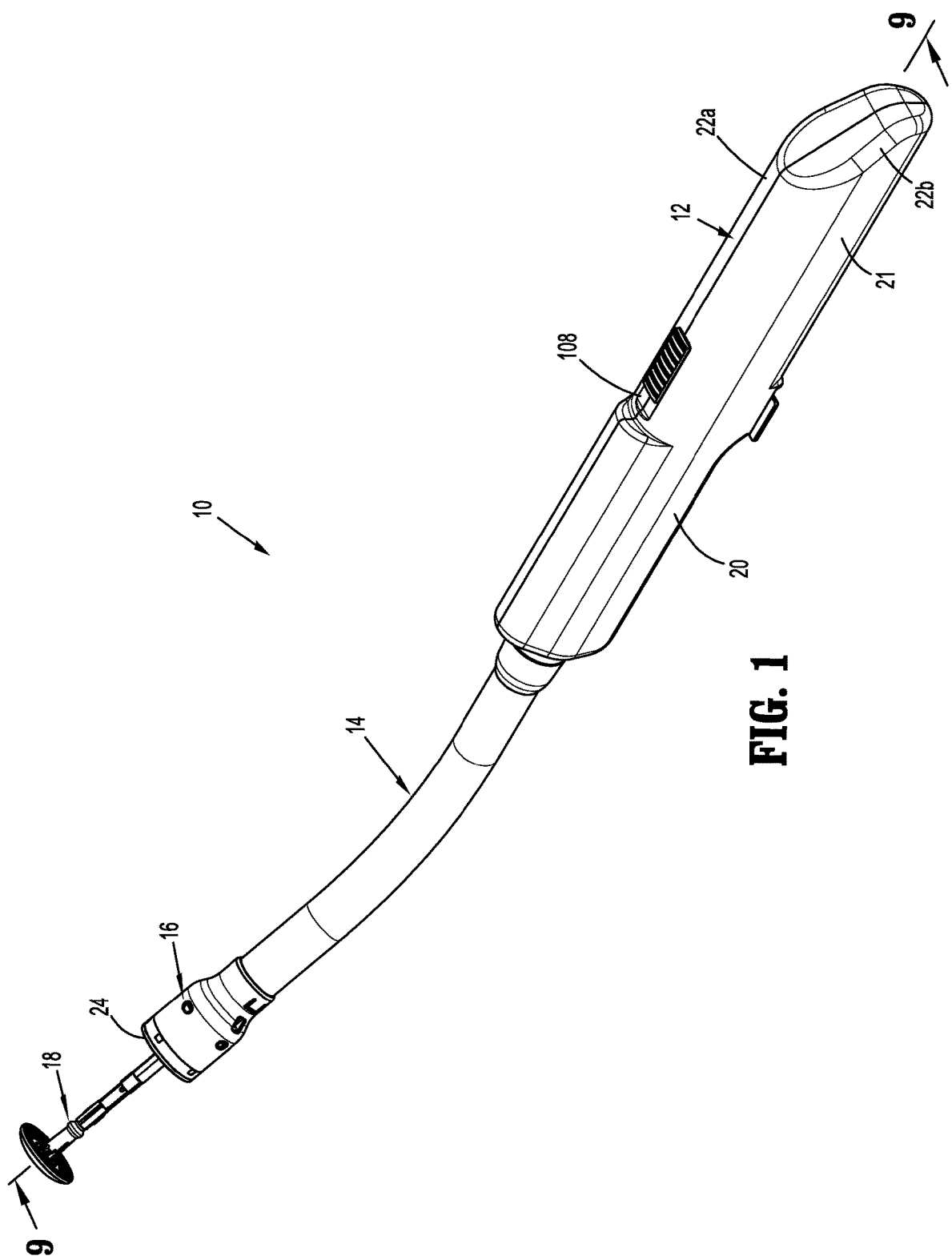
FIG. 1 is a side perspective view of an exemplary embodiment of the presently disclosed powered circular stapling device with the stapling device in an unclamped position.

The presently disclosed circular stapling device will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "clinician" is used generally to refer to medical personnel including doctors, nurses, and support personnel.

Referring to FIG. 1, the presently disclosed powered circular stapling device is shown generally as stapling device 10 and includes a handle assembly 12, an elongate body 14, a shell assembly 16, and an anvil assembly 18. The handle assembly 12 includes a housing 20 that defines a grip portion 21. The housing 20 may be formed from half-sections 22a, 22b that are secured together using any of a variety of fastening devices including welds, adhesives, screws or the like. In embodiments, the housing 20 may be formed from a polymer such as thermo-plastic polymer. Alternately, other materials of construction are envisioned, e.g., metal.

The elongate body 14 has a proximal end portion connected to the housing 20 of the handle assembly 12 and a distal end portion that supports the shell assembly 16. The shell assembly 16 includes a staple cartridge 24 that supports an annular array of staples 24a (FIG. 9). The anvil assembly 18 is supported on a distal end of an approximation mechanism 26 (FIG. 15). The approximation mechanism 26 is operable to move the anvil assembly 18 in relation to the shell assembly 16 between unclamped and clamped positions. The shell assembly 16 includes a pusher 27 (FIG. 19) that is coupled to a firing mechanism 28 and is movable from a retracted position to an advanced position to eject staples 24a (FIG. 9) from the staple cartridge 24. For a more detailed description of the shell assembly 16, the anvil assembly, and the approximation and firing mechanisms, see U.S. Pat. No. 7,303,106 (the '106 Patent), U.S. Pat. No. 6,957,758 (the '758 Patent), and U.S. Pat. No. 9,307,994 (the '994 Patent) which are incorporated herein in their entirety by reference.

Figure 2:
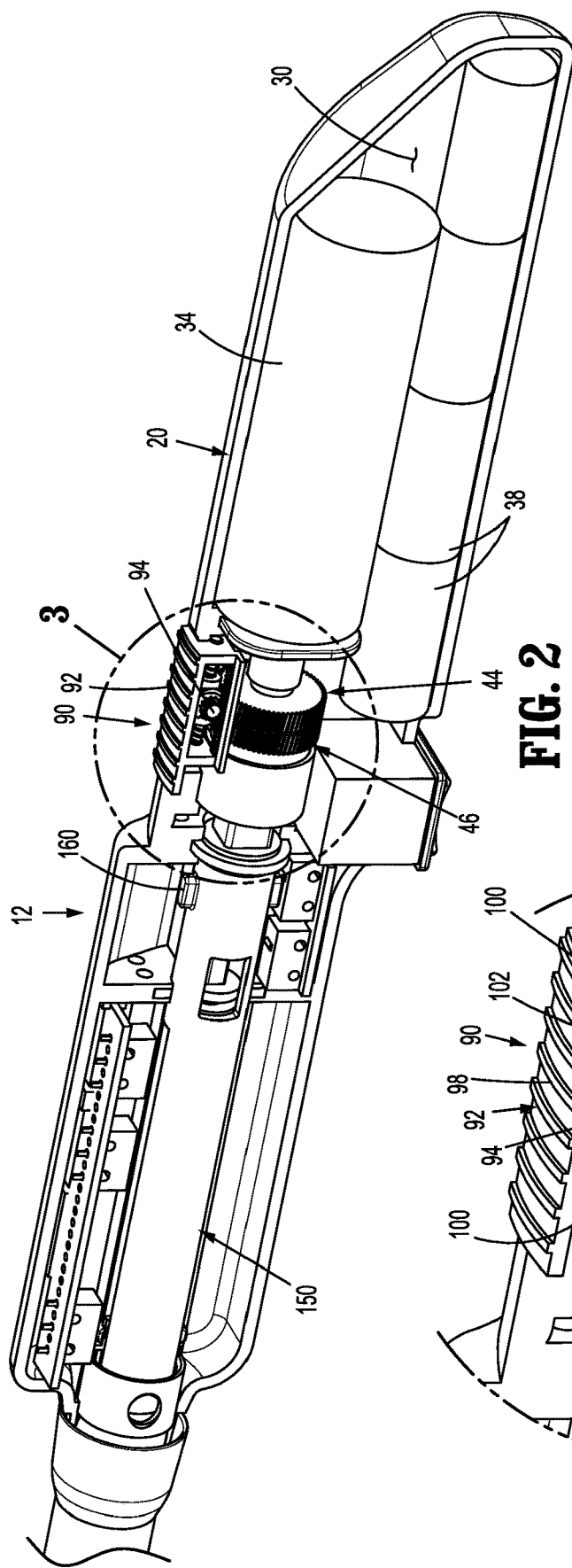
FIG. 2 is a side perspective view of a handle assembly of the stapling device shown in FIG. 1 with a handle half-section removed.
Figure 3:
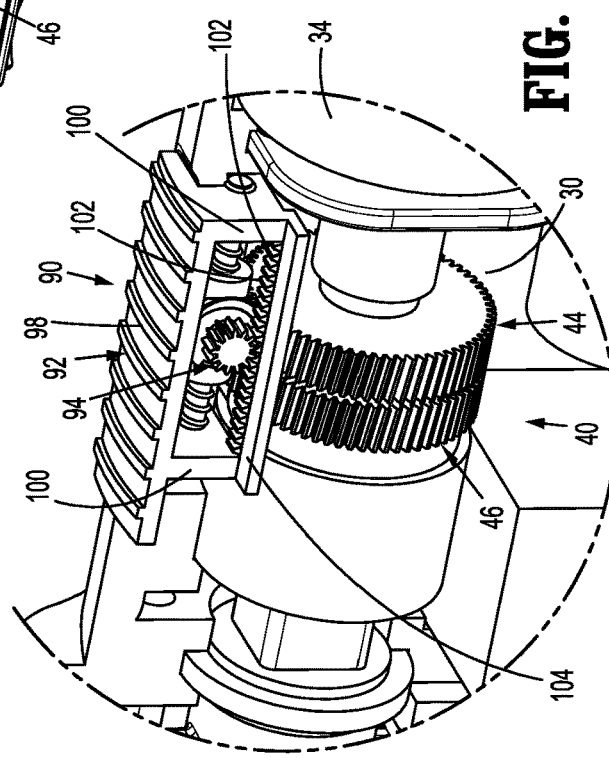
FIG. 3 is an enlarged view of the indicated area of detail shown in FIG. 2.
Figure 4:
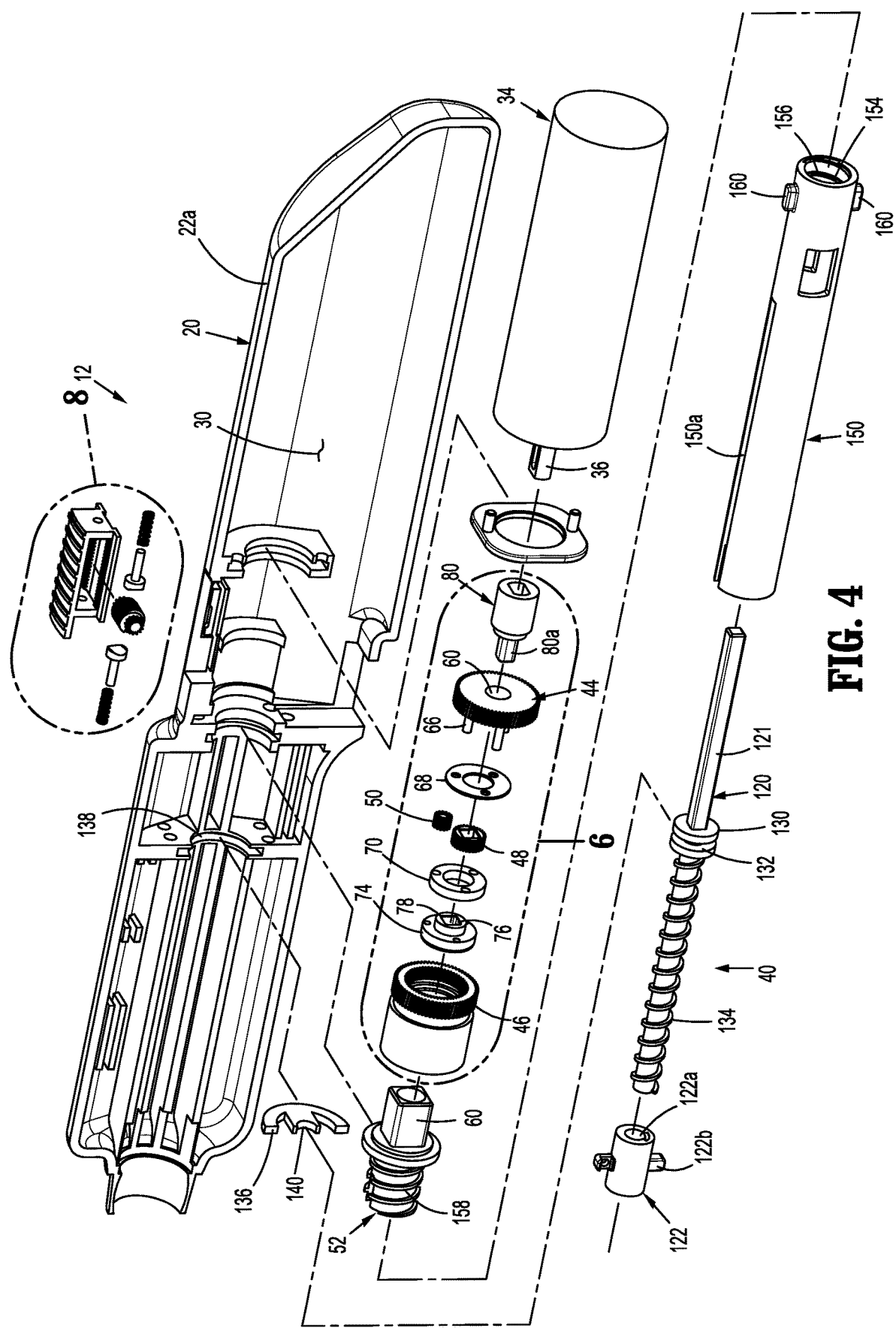
FIG. 4 is a side perspective exploded view of the handle assembly shown in FIG. 2.

Referring to FIGS. 2-4, the housing 20 of the handle assembly 12 defines a cavity 30 that receives a motor 34 having a drive shaft 36 (FIG. 4). The cavity 30 also receives batteries 38 (FIG. 2) for powering the motor 34. Alternately, the motor 34 may be connected to an external power source (not shown) by an electrical cable (not shown). The drive shaft 36 (FIG. 4) of the motor 34 is coupled to a transmission assembly 40 that is operable to selectively direct power from the motor 34 to the approximation mechanism 26 (FIG. 15) or the firing mechanism 28 (FIG. 19) as described in further detail below to selectively control clamping and firing of the stapling device 10. The drive shaft 36 of the motor 34 is rotatable in response to actuation of the motor 34 to drive the transmission assembly 40 and the approximation and firing mechanisms 26 and 28, respectively, as described in further detail below.

Figure 7:
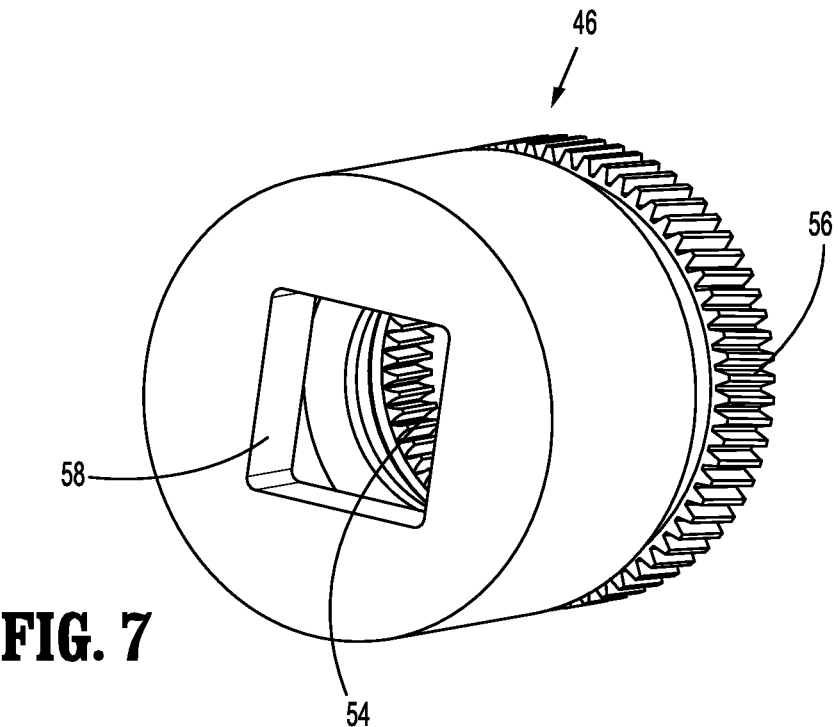
FIG. 7 is a side perspective view of a fire gear of the transmission assembly of the handle assembly shown in FIG. 4.

Referring also to FIGS. 5-7, the transmission assembly 40 includes a clamp gear 44 (FIG. 5), a fire gear 46 (FIG. 7), a sun gear 48 (FIG. 6), a planetary gear 50 (FIG. 6), and a firing drive member 52 (FIG. 4). The fire gear 46 is cylindrical and includes a proximal portion and a distal portion. The proximal portion of the fire gear 46 has an internal gear surface 54 and an external gear surface 56. The distal portion of the fire gear 56 is cylindrical and is configured to be coupled to a proximal portion of the firing drive member 52 such that rotation of the fire gear 46 causes corresponding rotation of the firing drive member 52. In embodiments, the distal portion of the fire gear 56 defines a rectangular slot 58 (FIG. 7) that receives a rectangular proximal extension 60 (FIG. 4) of the firing drive member 52 to couple the firing drive member 52 to the proximal portion of the fire gear 46. The internal gear surface 54 of the fire gear 46 is engaged with the planetary gear 50.

The clamp gear 44 (FIG. 5) includes an annular body defining a through bore 62 and having an external gear surface 64. The annular body of the clamp gear 44 supports a plurality of posts 66 that extend proximally from the annular body. One of the posts 66 supports the planetary gear 50. The posts 66 are positioned about the sun gear 48 and extend through openings 68a (FIG. 6) in a spacer 68, openings 70a (FIG. 6) in a bearing 70, and openings 74a (FIG. 6) in a clamping disk 74 to fixedly secure the components together such that rotation of the clamp gear 44 causes corresponding rotation of the clamping disk 74. Although three posts 66 are illustrated, it is envisioned that the clamp gear 44 may include two or more posts 66.

Figure 11:
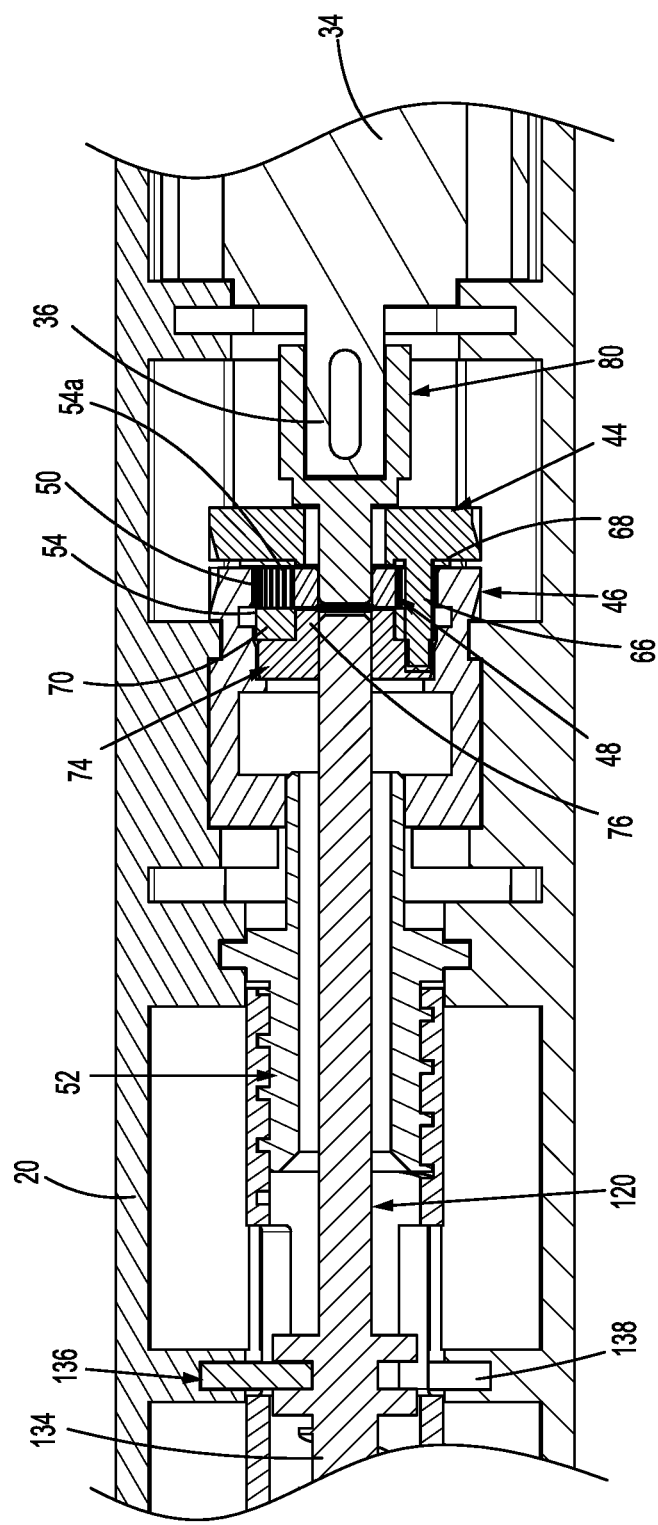
FIG. 11 is a cross-sectional view taken along section line 11-11 of FIG. 10.

Referring also to FIG. 11, the spacer 68 is positioned between the clamp gear 44 and the fire gear 46. The sun gear 48 is positioned within a through bore 54a (FIG. 6) defined by the internal gear surface 54 of the fire gear 46 and is engaged with the planetary gear 50 such that rotation of the sun gear 48 causes rotation of the planetary gear 50. As discussed above, the planetary gear 50 is engaged with the internal gear surface 54 of the fire gear 46. In embodiments, the clamping disk 74 includes a central hub 76 that defines a rectangular bore 78 (FIG. 6). The bearing 70 is received about the central hub 76 of the clamping disk 74 and the clamping disk 74 and the bearing 70 are supported within the fire gear 46 at a position distally of the sun gear 48.

The drive shaft 36 (FIG. 4) of the motor 34 is coupled to the sun gear 48 such that rotation of the drive shaft 36 causes corresponding rotation of the sun gear 48. In embodiments, the transmission assembly 40 also includes a motor drive link 80 (FIG. 4) that couples the drive shaft 36 of the motor 34 to the sun gear 48. In embodiments, the sun gear 48 defines a rectangular opening 84 (FIG. 6) and the motor drive link 80 includes a rectangular extension 80a that extends through the through bore 62 of the clamp gear 44 and is received within a rectangular bore 84 formed in the sun gear 48 to secure the motor drive link 80 to the sun gear 48. In some embodiments, the motor drive link 80 includes a non-circular opening 86 (FIG. 6) that receives a motor drive shaft 36 to couple the motor drive shaft 36 to the motor drive link 80. Alternately, it is envisioned that the motor drive shaft 36 can be coupled directly to the clamping disk 74.

Figure 8:
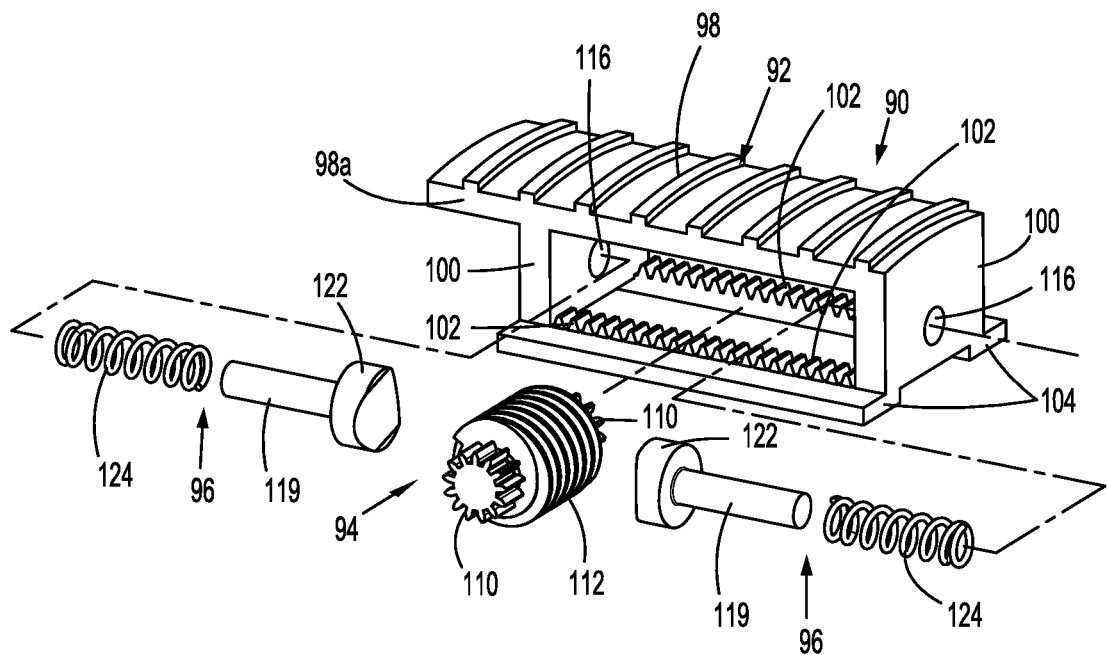
FIG. 8 is an enlarged view of the indicated area of detail shown in FIG. 4.
Figure 13:
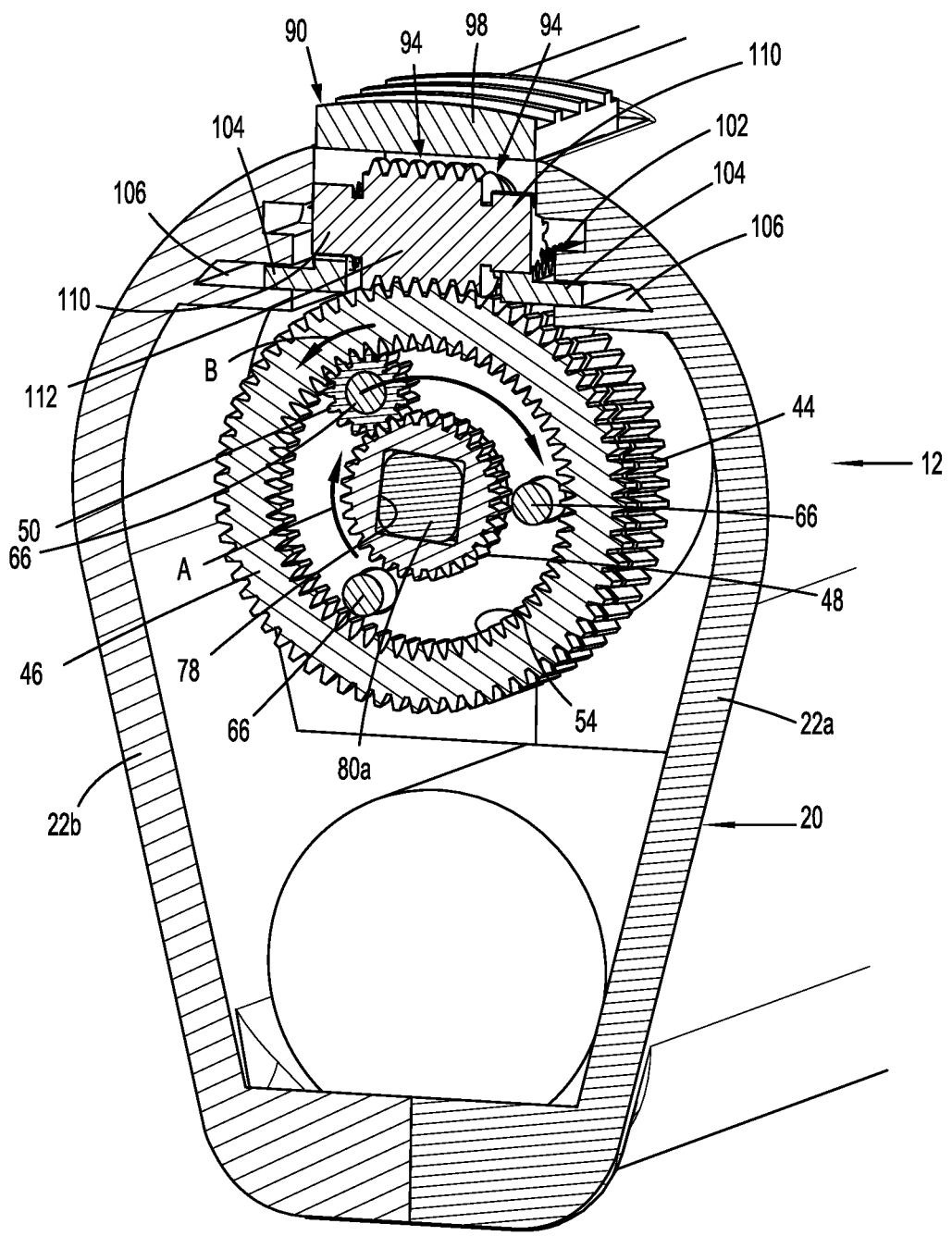
FIG. 13 is a cross-sectional view taken along section line 13-13 of FIG. 12.

Referring to FIGS. 2-4 and 8, a transfer switch assembly 90 (FIG. 8) is movably supported on the housing 20 of the handle assembly 12. The transfer switch assembly 90 includes a carriage 92, a worm gear assembly 94, and first and second biasing assemblies 96 (FIG. 8). The carriage 92 includes a finger engagement member 98, longitudinally spaced end walls 100, laterally spaced racks 102, and laterally spaced skis 104 (FIG. 8). The finger engagement member 98 is supported on an upper end of the end walls 100 and the spaced racks 102 are supported on a lower end of the end walls 100. The skis 104 extend outwardly from respective racks 102 and are received within elongated slots 106 (FIG. 13) defined within the housing 20 of the handle assembly 12 to facilitate longitudinal movement of the carriage 92 within the housing 20 between first and second positions. An outer surface of the housing 20 defines a recess 108 (FIG. 1) that receives a distal extension 98a (FIG. 8) of the finger engagement member 98 to confine the carriage 92 to linear movement along the housing 20.

Referring to FIG. 8, the worm gear assembly 94 is supported within the carriage 92 between the finger engagement member 98 and the spaced racks 102 of the carriage 92. More specifically, the worm gear assembly 94 includes support gears 110 and a worm gear 112. Each of the support gears 110 is positioned at one end of the worm gear 112 and is received on a respective one of the spaced racks 102 to support the worm gear 112 at a position that is axially aligned with the external gear surfaces of the 56 and 64 of the fire gear 46 and the clamp gear 44, respectively (FIG. 3). The carriage 92 is movable within and along the housing 20 from a first position in which the worm gear 112 is engaged with the fire gear 46 (FIG. 12) to a second position (FIG. 17) in which the worm gear 112 is aligned with the clamp gear 44. When carriage 92 is in the first position with the worm gear 112 engaged with the clamp gear 44, the clamp gear 44 is locked, i.e., prevented from rotating within the housing 20. Similarly, when the carriage 92 is in the second position with the worm gear 112 engaged with the fire gear 46, the fire gear 46 is locked or prevented from rotating within the housing 20.

Each of the longitudinally spaced end walls 100 of the carriage 92 defines a bore 116. Each of the biasing assemblies 96 of the transfer switch assembly 90 includes a post 119, a head portion 122, and a coil spring 124. The post 119 is received within a respective one of the bores 116 in an end wall 100 and the spring 124 is positioned about the post 119 between the respective end wall 100 and the head portion 122 to urge the head portion 122 towards and into engagement with the worm gear 112. When the carriage 92 is moved from the first position to the second position or vice-versa, if teeth on the worm gear 112 are not aligned with teeth on the respective fire gear 46 or clamp gear 44, longitudinal translation of the worm gear 112 will be blocked by the respective fire or clamp gear 46, 44. As such, movement of the worm gear 112 within the carriage 92 is prevented such that the carriage 92 will move longitudinally independently of the worm gear 112 as the carriage 92 is translated along the housing 20. When carriage 92 moves independently of the worm gear 112 along the housing 20, one of the springs 124 of a respective one of the biasing assemblies 96 will compress as the worm gear approaches an end wall 100 of the carriage 92 and the support gears 110 will rotate as the support gears 110 move along the racks 102 to rotate the worm gear 112. As soon as the teeth of the worm gear are aligned with the teeth of the respective fire or clamp gear 46, 44, the compressed spring 124 of the respective biasing assembly 96 will urge the worm gear 112 into engagement with the respective fire or clamp gear 46, 44 to lock the respective fire or clamp gear 46, 44.

Referring to FIGS. 4, 9-11, and 14, the approximation mechanism 26 includes a clamping rod 120, a clamping member 122, a clamping extension 124, a pair of flexible bands 126 and an anvil retainer 128 (FIG. 9). The clamping rod 120 includes a proximal portion 121 having a rectangular configuration, a central hub portion 130 defining an annular slot 132, and a distal threaded portion 134. The proximal portion 121 is received within the rectangular bore 78 (FIG. 4) of the clamping disk 74 such that rotation of the clamping disk 74 causes rotation of the clamping rod 120.

The clamping member 122 defines a longitudinal through bore 122a that receives the distal threaded portion 134 of the clamping rod 120. The longitudinal through bore 122a of the clamping rod 120 is threaded such that rotation of the clamp rod 120 causes the distal threaded portion 134 to rotate within the clamping member 122 to advance the clamping member 122 within the housing 20 of the handle assembly 12 (FIG. 9). The clamping member 122 includes fins 122b that are received in elongate slots 150a (FIG. 4) formed in a firing connector 150 of the firing mechanism 28 as described below to prevent rotation of the clamping member 122 within the housing 20 of the handle assembly 12.

A clip 136 (FIG. 11) is supported within a slot 138 (FIG. 4) in the housing 20 of the handle assembly 12. The clip 136 includes a finger 140 that is received in the slot 132 of the central hub portion 130 of the clamping rod 120 to prevent longitudinal movement of the clamping rod 120 within the housing 20 of the handle assembly 12. Since the slot 132 of the central hub portion 130 of the clamping rod 120 is annular, the clamping rod 120 is free to rotate within the housing 20 with the clamping disk 74.

The clamping member 122 has a distal portion 144 (FIG. 14) that is coupled to the clamping extension 124 such that longitudinal movement of the clamping member 12 within the housing 20 of the handle assembly 12 causes longitudinal movement of the clamping extension 124 within the elongate body 14 (FIG. 14). The clamping extension 124 has a distal portion that is coupled to the flexible bands 126 such that longitudinal movement of the clamping extension 124 causes longitudinal movement of the flexible bands 126. The flexibility of the bands 126 facilitates movement of the bands 126 through the curved elongate body 14. The anvil retainer 128 (FIG. 9) is secured to the distal portion of the flexible bands 126 such that longitudinal movement of the flexible bands 126 causes longitudinal movement of the anvil retainer 128 which supports the anvil assembly 18 (FIG. 9). In embodiments, the housing 20 of the handle assembly supports a limit switch 142 (FIG. 14A). The clamping member 122 is coupled to an engagement member 143 that is positioned to engage the limit switch 142 when the clamping member 122 moves to a predetermined axial position within the housing 20 of the handle assembly 12 to shut down the motor 34. For a more detailed description of the a known approximation mechanism including flexible bands and an anvil retainer, see the '106, '758, and '994 Patents.

Referring to FIGS. 4, 9-11, and 14, the firing mechanism includes the firing connector 150, a connector extension 152, and the pusher 27 (FIG. 19. The firing connector 150 defines a longitudinal bore 154 that includes a threaded proximal portion 156 (FIG. 14). The firing drive member 52 includes a threaded distal portion 158 (FIG. 4) that is received within the proximal portion 156 of the of the firing connector 150 such that rotation of the firing drive member 52 causes longitudinal movement of the firing connector 150 within the housing 20 of the handle assembly 12. The firing connector 150 includes wings 160 that are positioned to actuate a limit switch 162 (FIG. 10) supported within the housing 20 of the handle assembly 12. The limit switch 162 shuts the motor 34 off when the firing connector 150 reaches a predetermined longitudinal position within the housing 20 and engages the limit switch 162.

The distal portion of the firing connector 150 is secured to a proximal end of the connector extension 152 and the distal end of the connector extension 152 is secured to the pusher 27 (FIG. 19) located within the shell assembly 16. When the firing drive member 52 is rotated by the firing gear 46, the firing connector 150 is moved longitudinally to cause corresponding longitudinal movement of the connector extension 152 (FIG. 14) and the pusher 27 to eject staples 24a (FIG. 9) from the staple cartridge 24.

Figure 12:
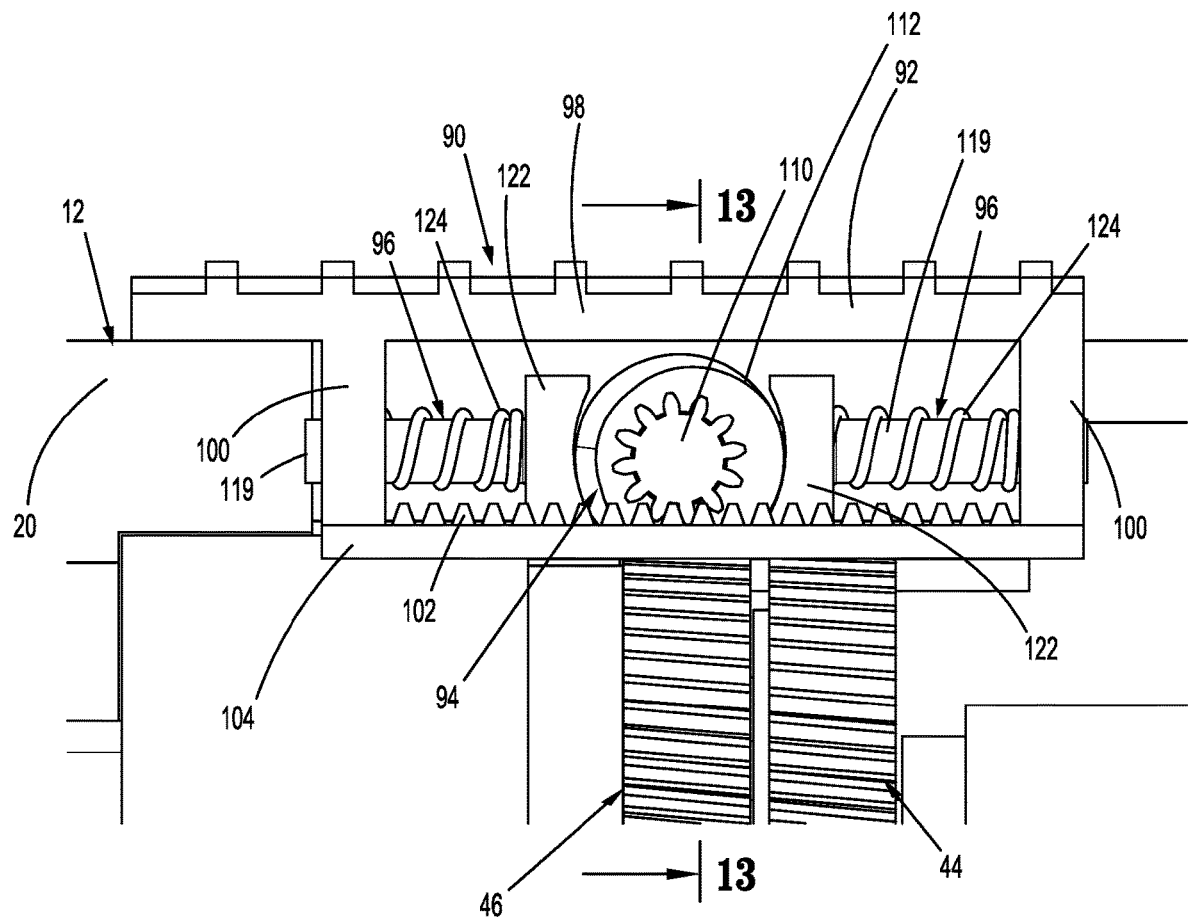
FIG. 12 is a side view of a power transfer switch assembly of the handle assembly shown in FIG. 4 in the clamping mode.

Referring to FIG. 12, when the transfer switch assembly 90 is in the first position such that the stapling device 10 is in the clamping mode, the worm gear 112 of the worm gear assembly 94 is engaged with the fire gear 46 to prevent rotation of the fire gear 46 within the housing 20 of the handle assembly 12. Referring also to FIGS. 13-16, in the clamping mode, when the motor 34 is activated, such as by pressing a button (not shown) on the handle assembly 12, the sun gear 48 rotates in the direction indicated by arrow "A" in FIG. 13 to rotate the planetary gear 50 in the direction indicated by arrow "B". As discussed above, the planetary gear 50 is engaged with the internal gear surface 54 of the fire gear 46. Since the fire gear 46 is locked by the worm gear 112 of the transfer switch assembly 90 in the clamping mode and cannot rotate, engagement between the planetary gear 50 and the internal gear surface 54 of the fire gear 46 causes the planetary gear 50 to push on the post 66 of the clamp gear 44 (FIG. 13) supporting the planetary gear 50 to cause the clamp gear 44 to rotate within the housing 20.

As discussed above, the posts 66 of the clamp gear 44 connect the clamp gear 44 to the clamping disk 74. Thus, as the clamp gear 44 rotates within the housing 20 of the handle assembly 12, the clamping disk 74 also rotates within the housing 20. Rotation of the clamping disk 74 causes rotation of the clamping rod 120 (FIG. 10), which in turn causes the clamping member 122 (FIG. 14) to move longitudinally within the housing 20 to move the clamping extension 124, the flexible bands 126, the anvil retainer 128, and the anvil assembly 18 that is supported on the anvil retainer 128 longitudinally in the direction indicated by arrow "C" in FIGS. 14 and 16. It is noted that the motor 34 can be reversed to move the anvil assembly 18 in a direction opposite to the direction indicated by arrow "C"

Figure 17:
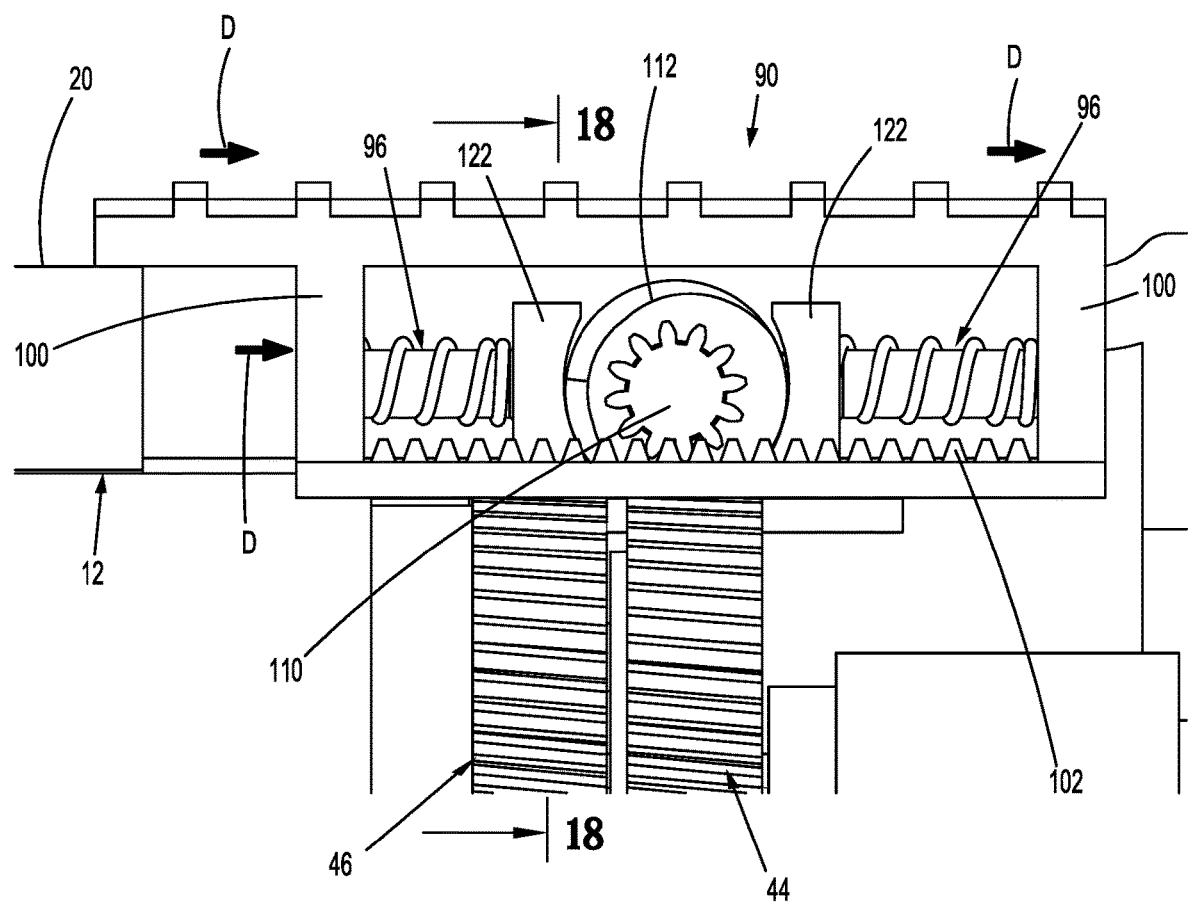
FIG. 17 is a side view of the power transfer switch assembly of the handle assembly shown in FIG. 4 in the firing mode.

Referring to FIG. 17, after the stapling device 10 is moved to the clamped position (FIG. 16) and a clinician wants to fire the stapling device 10, the transfer switch assembly 90 can be moved to the second position to place the stapling device 10 in a firing mode. To move the stapling device to the firing mode, the carriage 92 is pushed in the direction indicated by arrows "D" to move the worm gear 112 into engagement with the clamp gear 44. When the worm gear 112 engages the clamp gear 44, the clamp gear 44 is locked and can no longer rotate within the housing 20 of the handle assembly 12.

Figure 18:
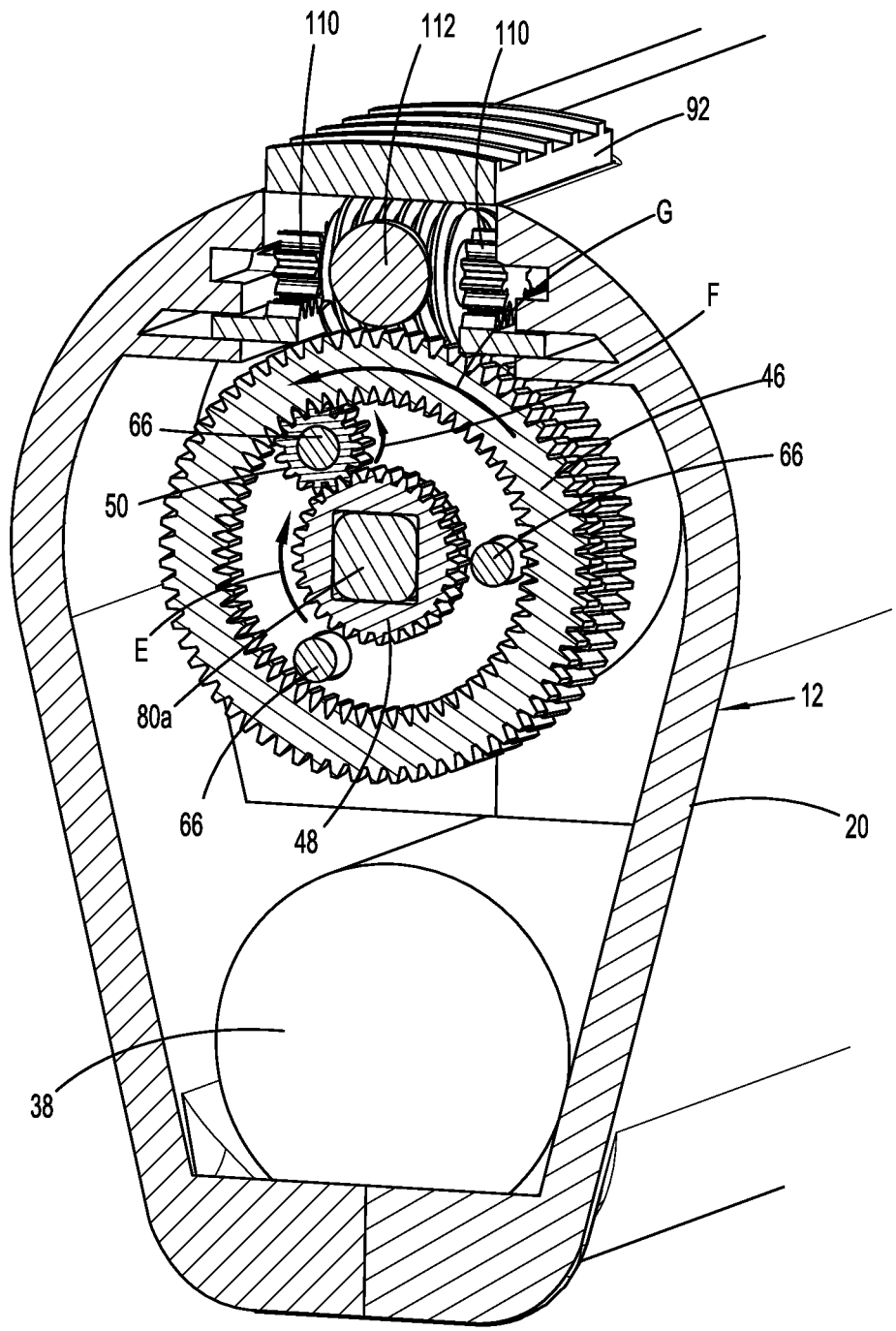
FIG. 18 is a cross-sectional view taken along section line 18-18 of FIG. 17.

Referring to FIGS. 18-20, when the motor 34 (FIG. 19) is activated with the transfer switch assembly 90 in the second position and the stapling device 10 in the firing mode, the motor 34 rotates the sun gear 48 in the direction indicated by arrow "E" in FIG. 18 to rotate the planetary gear 50 in the direction indicated by arrow "F". The planetary gear 50 engages the internal gear surface 54 of the fire gear 44. Since the fire gear 44 is no longer locked, rotation of the planetary gear 50 rotates the fire gear 46 in the direction indicated by arrow "G" in FIG. 18.

The firing drive member 52 is coupled to the fire gear 46 such that rotation of the fire gear 46 causes corresponding rotation of the firing drive member 52. As discussed above, the threaded distal portion 158 of the firing drive member 52 is received within the threaded proximal portion 156 of the firing connector 150 such that rotation of the firing drive member 52 causes longitudinal movement of the firing connector 150. Longitudinal movement of the firing connector 150 causes corresponding longitudinal movement of the connector extension 152 (FIG. 19) and the pusher 27 to eject staples 24a (FIG. 9) from the staple cartridge 24. After firing of the stapling device 10, the transfer switch 90 can be returned to the clamping mode and the motor 34 can be actuated to return the stapling device 10 to the unclamped position.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed:

1. A circular stapling device comprising:
   a handle assembly including a housing, a motor, and a transmission assembly, the housing defining a cavity, the motor supported within the cavity and having a drive shaft coupled to the transmission assembly, the transmission assembly including a fire gear, a clamp gear, a sun gear, and a planetary gear, the fire gear including an annular body having an internal gear surface and an external gear surface, the clamp gear including an external gear surface and at least one post that rotatably supports the planetary gear, wherein the drive shaft of the motor is coupled to the sun gear, the sun gear is engaged with the planetary gear, and the planetary gear is engaged with the internal gear surface of the fire gear;
   a transfer switch assembly supported by the housing of the handle assembly, the transfer switch assembly being movable between a first position engaged with the fire gear to prevent rotation of the fire gear and a second position engaged with the clamp gear to prevent rotation of the clamp gear;
   an elongate body having a proximal portion coupled to the handle assembly and a distal portion;
   a shell assembly supported on the distal portion of the elongate body, the shell assembly including a staple cartridge having an annular array of staples and a pusher;
   an anvil assembly operably coupled to the clamp gear; and
   wherein the transmission assembly is configured such that activation of the motor with the transfer switch assembly in the first position causes movement of the anvil assembly in relation to the staple cartridge and activation of the motor with the transfer switch in the second position causes movement of the pusher in relation to the staple cartridge to eject staples from the staple cartridge.

2. The circular stapling device of claim 1, wherein the transfer switch assembly includes a worm gear assembly including a worm gear, the worm gear being engaged with the fire gear in the first position of the transfer switch and engaged with the clamp gear in the second position of the transfer switch.

3. The circular stapling device of claim 2, wherein the transfer switch assembly includes a carriage supported by the housing of the handle assembly, the carriage being movable in relation to the transmission assembly to move the transfer switch assembly between the first and second positions.

4. The circular stapling device of claim 3, wherein the worm gear assembly includes a support gear positioned on each end of the worm gear and the carriage includes spaced racks, the support gears being movable on the spaced racks to support the worm gear on the carriage.

5. The circular stapling device of claim 3, wherein the transfer switch assembly includes first and second biasing mechanisms supported on the carriage, the first biasing mechanism being positioned to engage a first side of the worm gear assembly to urge the worm gear assembly in a first direction and the second biasing mechanism being positioned to engage a second side of the worm gear assembly opposite of the first side of the worm gear assembly to urge the worm gear assembly in a second direction opposite to the first direction, wherein the first and second biasing mechanisms allows the worm gear assembly to move in relation to the carriage when the worm gear is misaligned with the external gear surface of one of the fire gear and the clamp gear as the transfer switch assembly is moved between the first and second positions.

6. The circular stapling device of claim 5, wherein the spaced racks include rack teeth that are engaged with the support gears of the worm gear assembly to cause rotation of the support gears when the carriage is moved in relation to the worm gear assembly, wherein rotation of the support gears causes rotation of the worm gear to move the worm gear into alignment with the external gear surface of the fire gear or the clamp gear as the transfer switch assembly is moved between the first and second positions.

7. The circular stapling device of claim 3, wherein the carriage includes a finger engagement member, the finger engagement member being supported on an outer surface of the housing.

8. The circular stapling device of claim 1, wherein the transmission assembly further includes a clamping disk and the clamp gear includes a plurality of posts, the planetary gear being supported on one of the plurality of posts, and the plurality of posts extending through the clamping disk to secure the clamping disk to the clamp gear such that rotation of the clamp gear causes rotation of the clamping disk.

9. The circular stapling device of claim 8, wherein the clamping disk is coupled to a clamping rod and the clamping rod supports a clamping member, the clamping rod having a distal threaded portion and the clamping member defines a threaded bore, the distal threaded portion of the clamping rod being received within the threaded bore of the clamping member such that rotation of the clamping rod causes longitudinal movement of the clamping member, the clamping member being coupled to the anvil assembly such that longitudinal movement of the clamping member causes longitudinal movement of the anvil assembly.

10. The circular stapling device of claim 9, wherein the handle assembly includes a limit switch positioned to limit movement of the clamping member within the housing.

11. The circular stapling device of claim 1, wherein the fire gear is coupled to a firing drive member such that rotation of the fire gear causes rotation of the firing drive member.

12. The circular stapling device of claim 11, further including a firing connector defining a threaded bore, wherein the firing drive member includes a threaded distal portion that is received within the threaded bore of the firing connector such that rotation of the firing drive member causes longitudinal movement of the connector extension, the connector extension being coupled to the pusher.

13. The circular stapling device of claim 12, wherein the handle assembly includes a limit switch positioned to limit movement of the firing connector within the housing.

14. The circular stapling device of claim 1, wherein handle assembly includes batteries to power the motor.

15. A transfer switch assembly comprising:
a carriage having first and second spaced end walls, a finger engagement surface extending between an upper end of the first and second end walls, and spaced racks extending between a lower end of the spaced end walls;
a worm gear assembly positioned between the spaced racks, the worm gear assembly including a worm gear having gear teeth, and a support gear positioned on each end of the worm gear, the support gears being movable on the spaced racks to movably support the worm gear between the spaced racks on the carriage; and
first and second biasing mechanisms supported on the carriage, the first biasing mechanism being positioned to engage a first side of the worm gear assembly to urge the worm gear assembly in a first direction on the carriage and the second biasing mechanism being positioned to engage a second side of the worm gear assembly opposite to the first side of the worm gear assembly to urge the worm gear assembly in a second direction on the carriage opposite to the first direction.

16. The transfer switch assembly of claim 15, wherein the carriage is configured to move in relation to a transmission assembly of a device between a first position in which the gear teeth of the worm gear are engaged with gear teeth of a first gear of the transmission assembly and a second position in which the gear teeth of the worm gear are engaged with gear teeth of a second gear of the transmission assembly, the first and second biasing mechanisms being configured to allow the worm gear assembly to move in relation to the carriage when the gear teeth of the worm gear are misaligned with the gear teeth of the first second gears of the transmission assembly, wherein movement of the carriage in relation to the worm gear assembly causes rotation of the support gears to rotate the gear teeth of the worm gear into alignment with the gear teeth of one of the first and second gears of the transmission assembly.

* * * * *